(12) United States Patent
Durin et al.

(10) Patent No.: US 8,703,434 B2
(45) Date of Patent: Apr. 22, 2014

(54) DEVICE AND METHOD FOR ISOLATING BIOLOGICAL OR CHEMICAL TARGETS

(75) Inventors: Guillaume Durin, Gif sur Yvette (FR); Sylvaine Chabaud, Ville-sous-Anjou (FR); Cyril Delattre, Izeaux (FR); Dorothée Jary, Sassenage (FR)

(73) Assignee: Commissariat a l'Energie Atomique et aux Energies Alternatives, Paris (FR)

( * ) Notice: Subject to any disclaimer, the term of this patent is extended or adjusted under 35 U.S.C. 154(b) by 27 days.

(21) Appl. No.: 13/321,177

(22) PCT Filed: May 17, 2010

(86) PCT No.: PCT/FR2010/000374
§ 371 (c)(1),
(2), (4) Date: Dec. 21, 2011

(87) PCT Pub. No.: WO2010/133776
PCT Pub. Date: Nov. 25, 2010

(65) Prior Publication Data
US 2012/0190037 A1    Jul. 26, 2012

(30) Foreign Application Priority Data

May 19, 2009 (FR) ..................... 09 02383

(51) Int. Cl.
| | |
|---|---|
| *G01N 33/53* | (2006.01) |
| *G01N 33/567* | (2006.01) |
| *C12Q 1/68* | (2006.01) |
| *C12Q 1/04* | (2006.01) |
| *C12P 19/34* | (2006.01) |
| *C12M 1/00* | (2006.01) |
| *C12M 1/34* | (2006.01) |
| *C12M 3/00* | (2006.01) |
| *G01N 15/06* | (2006.01) |
| *G01N 33/00* | (2006.01) |
| *G01N 33/48* | (2006.01) |

(52) U.S. Cl.
USPC ............. 435/7.2; 435/6.1; 435/6.11; 435/7.1; 435/34; 435/91.1; 435/283.1; 435/287.1; 435/287.2; 422/50; 422/68.1

(58) Field of Classification Search
USPC ......... 435/6.1, 6.11, 7.1, 283.1, 287.1, 287.2, 435/7.2, 34; 422/50, 68.1; 536/23.1; 530/300, 350
See application file for complete search history.

(56) References Cited

U.S. PATENT DOCUMENTS

| | | |
|---|---|---|
| 4,628,037 A | 12/1986 | Chagnon et al. |
| 2003/0015028 A1 | 1/2003 | Mukaiyama |
| 2005/0013741 A1 | 1/2005 | a'Brassard |
| 2006/0141450 A1 | 6/2006 | Zhang et al. |
| 2006/0252031 A1 | 11/2006 | Abbott et al. |

FOREIGN PATENT DOCUMENTS

| | | |
|---|---|---|
| WO | WO 2004/053115 A1 | 6/2004 |
| WO | WO 2007/097740 A2 | 8/2007 |
| WO | WO 2008/131554 A1 | 11/2008 |

OTHER PUBLICATIONS

International Search Report from International Patent Application No. PCT/FR2010/000374, filed May 17, 2010.
Anonyme: "Pathatrix Overvieuw"; Matrix Microscience Product Details, May 3, 2008; XP002563982; URL:http://matrixmsci.com/pathatrix.htm.

*Primary Examiner* — Frank Lu
(74) *Attorney, Agent, or Firm* — Alston & Bird LLP (57) ABSTRACT

The present invention relates to a device for collecting and concentrating biological or chemical targets with a view to detecting same, wherein the device comprises a reaction chamber (1) in which functionalized magnetic beads (2) are placed, an ultrasonic agitation system (3), a magnetic field (4) that can be activated (ON position) or inactivated (OFF position), and a fluid movement system (5) for feeding (51) and discharging (52) a portion or the entirety of the contents of the reaction chamber.
The present invention also relates to a method for capturing biological or chemical targets using said device.

13 Claims, 4 Drawing Sheets

SEQUENCE LISTING

```
<160> NUMBER OF SEQ ID NOS: 6

<210> SEQ ID NO 1
<211> LENGTH: 20
<212> TYPE: DNA
<213> ORGANISM: Escherichia coli

<400> SEQUENCE: 1
catgccgcgt gtatgaagaa                                            20

<210> SEQ ID NO 2
<211> LENGTH: 21
<212> TYPE: DNA
<213> ORGANISM: Escherichia coli
```

-continued

```
<400> SEQUENCE: 2
cgggtaacgt caatgagcaa a                                              21

<210> SEQ ID NO 3
<211> LENGTH: 31
<212> TYPE: DNA
<213> ORGANISM: Escherichia coli

<400> SEQUENCE: 3
tattaacttt actcccttcc tccccgctga a                                   31

<210> SEQ ID NO 4
<211> LENGTH: 22
<212> TYPE: DNA
<213> ORGANISM: Bacillus subtilis

<400> SEQUENCE: 4
acgtgggtaa cctgcctgta ag                                             22

<210> SEQ ID NO 5
<211> LENGTH: 22
<212> TYPE: DNA
<213> ORGANISM: Bacillus subtilis

<400> SEQUENCE: 5
tagccgaagc cacctttat gt                                              22

<210> SEQ ID NO 6
<211> LENGTH: 28
<212> TYPE: DNA
<213> ORGANISM: Bacillus subtilis

<400> SEQUENCE: 6
taccggatgg ttgtttgaac cgcatggt                                       28
```

DEVICE AND METHOD FOR ISOLATING
BIOLOGICAL OR CHEMICAL TARGETS

FIELD OF THE INVENTION

The present invention relates to the field of the detection of biological or chemical targets on the basis of taking a liquid sample.

BACKGROUND OF THE INVENTION

More specifically, the objective of the present invention is to meet the need for collecting and/or concentrating biological or chemical targets and to thus be of use in the context of the detection of undesirable elements such as pathogenic microorganisms or chemical pollutants in samples such as river water, fluids of cooling towers, of domestic and drinking water supply networks, etc. The biological or chemical targets can be present in a very small amount in the samples and the detection thereof is then possible only by taking large volumes (greater than 50 ml).

The term "biological or chemical target" is intended to mean microorganisms, i.e. enveloped or nonenveloped viruses, gram-positive and gram-negative vegetative bacteria, bacteria in sporulated form, protozoa, microscopic fungi and yeasts, microplankton, pollen, animal cells and plant cells; it is also intended to mean chemical molecules (fertilizers, medicaments, pollutant chemical molecules such as byproducts of the chemical industry, phytosanitary products, etc.) or biochemical molecules (antigen, protein, hormones or endocrine system-disrupting compound, etc.).

It is known practice to use functionalized magnetic beads, i.e. magnetic beads bearing, at their surface, molecules capable of binding to desired targets, as a capture system intended for isolating and/or detecting biological or chemical targets, and various methods for capturing targets with magnetic beads have already been described; indeed, the advantage of using functionalized magnetic beads is that they have a large capture surface area, and that they can be easily recovered using a magnet and, optionally, reused after elution of the captured targets.

In particular, patent application US 2003/015028 describes a not very specific method for capturing microorganisms using a solid support to which a nutrient, in particular a carbohydrate, of said micro-organisms is bound; the solid support is preferably magnetic beads. The functioning of this method lies in the choice of the nutrient for capturing microorganisms.

patent application US 2006/0141450 describes a method for capturing cells, organelles or viruses present in samples of physiological origin using the not very specific properties of paramagnetic adsorption of magnetic beads.

The above methods are aimed at treating samples having a volume of approximately 1 ml; they are not suitable for the treatment of samples with a volume of greater than 50 ml.

International application WO 2008/131554 describes a device suitable for detecting pathogenic microorganisms using food samples; this device comprises a 500 ml Erlenmeyer flask placed on an agitating support equipped with a magnetic field. The use of this device provides for a prior step of culturing the sample in a selective culture medium suitable for the growth of the microorganisms being sought; next, these microorganisms are captured by means of magnetic particles onto which are grafted antibodies which bind to the microorganisms being sought. This very specific method for detecting microorganisms solves the problem of the small amount of biological targets in the sample through the culturing step, which makes it possible to multiply the microorganisms being sought and to thus facilitate the detection thereof. While it can be suitable for treating samples having a volume of a few tens of milliliters, its use nevertheless remains limited in terms of volume of the samples, since the problem then arises of obtaining good dispersion of the magnetic capture beads within the sample; finally, such a device is difficult to automate; it does not allow the treatment of several samples in series.

The same limits apply to the device for agitating and separating magnetic beads that is described in patent application US 2005/0013741; this device comprises two permanent magnets placed on either side of a container containing magnetic beads; these magnets are vertically mobile; depending on the movement that they are given, they can either agitate the beads in order to place them or maintain them in suspension, or group them back together in order to separate them from the sample. This device targets containers with a maximum volume of a few tens of milliliters. The problem encountered during the treatment of larger volumes is the difficulty in obtaining good dispersion of the magnetic beads and in subsequently recovering them.

Finally, the Pathatrix device from Matrix Microscience proposes the capture of targets such as pathogenic microorganisms in samples of 250 ml by circulating the sample in a loop in a tubular circuit in which functionalized magnetic capture beads are immobilized on a flat magnet. Since the beads are immobilized, this device produces a low capture yield which does not make it possible in particular to detect targets present at a low concentration.

Thus, it emerges from the aforementioned that no device of the prior art allows sensitive detection of targets present in a small amount in a liquid sample of large volume by means of automated processing.

SUMMARY OF THE INVENTION

The subject of the invention relates to an automatic device for processing a liquid sample having a volume V greater than or equal to 10 ml, preferably greater than or equal to 50 ml and more preferentially greater than or equal to 500 ml, comprising a reaction chamber, having a volume v of between 10 µl and 5 ml, in which functionalized magnetic beads are placed, said beads allowing the capture of biological or chemical targets in an amount such that the ratio of the capture surface area of the beads to the volume of the reaction chamber is between 0.2 and 200 $m^2/l$, preferably between 0.2 and 20 $m^2/l$ and even more preferably between 0.2 and 10 $m^2/l$, said reaction chamber being equipped:
- with a noninvasive agitation system enabling homogeneous dispersion of said beads;
- with a magnetic field that can be activated (ON position) or inactivated (OFF position);
- with a fluid movement system for feeding and discharging a portion or the entirety of the contents of the reaction chamber.

DETAILED DESCRIPTION OF THE INVENTION

Figure 1:
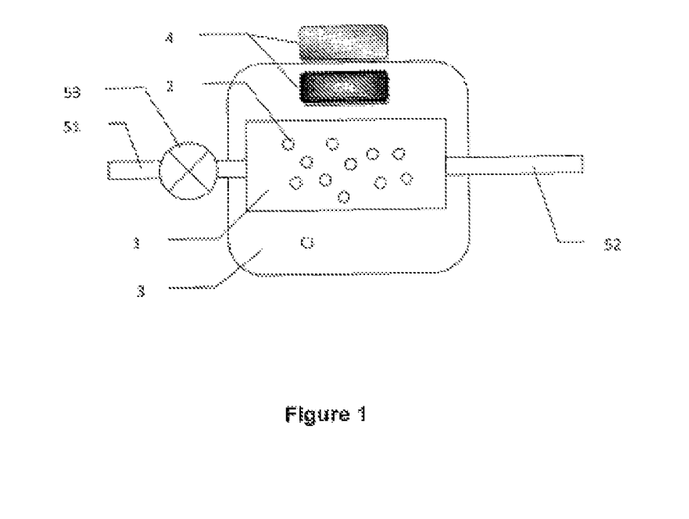
FIG. 1 is a diagrammatic representation of a device that is in accordance with the present invention.

FIG. 1 is a diagrammatic representation of the device according to the invention comprising a reaction chamber (1) in which functionalized magnetic beads (2) are placed, an agitation system, for example an ultrasonic bath (3), a magnetic field (4) that can be activated (ON position) or inactivated (OFF position), and a fluid movement system (5) for feeding (51) and discharging (52) a portion or the entirety of the contents of the reaction chamber.

The reaction chamber has a volume of preferably between 50 and 500 µl, and even more preferably 100 µl.

It can be in the form of a reservoir or else of a tubular system such as, for example, a capillary.

Preferably, the reaction chamber is coated with a hydrophobic surface so as to avoid adhesion of the capture beads to its internal walls; this hydrophobic surface is chosen from Teflon, ETFE (ethylene trifluoroethylene), PFA (perfluoroalkoxy copolymer resin) and PTFE (polytetrafluoroethylene).

The term "liquid sample" is intended to mean a specimen taken from industrial water (for example originating from a cooling circuit), from environmental water (watercourse, etc.), or else from drinking water intended for human or animal consumption, and by extension any sample in which the biological or chemical target(s) to be detected is (are) in solution or suspension. This sample may itself have been obtained from a specimen or other sample capable of containing the biological or chemical targets being sought, for example a food product, a body fluid, an air specimen, obtained by physical and/or chemical, and/or biological processing according to any method that can be adapted by those skilled in the art.

The device according to the invention has a capture capacity at very low concentrations of targets, it is therefore particularly suitable for processing liquid samples that may contain only a very small amount of biological or chemical targets; in particular, as regards biological targets, the device according to the invention is thus capable of detecting biological targets present in an amount less than or equal to 100 units per liter of sample, preferably in an amount less than or equal to 10 units per liter of sample, more preferably in an amount equal to one unit per liter of sample.

In order to avoid any exogenous contamination, the liquid samples are preferentially taken or prepared under conditions of great cleanliness with sterile equipment.

In the case of the analysis of the microbiological quality of air, the liquid samples are prepared according to techniques known to those skilled in the art (Stachowiak J C et al., Anal. Chem. 2007; 79 (15): 5763-70).

There is no theoretical limit to the maximum volume of said liquid sample; in practice, it does not generally exceed 10 l.

The fluid movement system for feeding and discharging a portion or the entirety of the contents of the reaction chamber makes it possible to feed a fraction of liquid sample into the reaction chamber with a view to capturing the biological or chemical targets, and then to discharge this fraction of liquid sample after the capture step. This system also makes it possible to feed the functionalized magnetic beads at the start and to discharge them at the end of the processing of the liquid sample.

In concrete terms, this fluid movement system preferably consists of a pressure regulation system (Fluigent) or a pump (53) such as a piston pump, a membrane pump or a peristaltic pump.

The agitation system enabling homogeneous dispersion of the beads is noninvasive, i.e. it does not require the introduction of an agitation accessory into the reaction chamber, thus avoiding the risk of contaminating the liquid sample.

It may be a system of agitation of the functionalized magnetic beads by means of a mobile magnetic field implemented by means of one or more rotating magnets; by moving the beads by causing the contents of the reaction chamber to move back and forth by means of the fluid movement system; or else by ultrasonic agitation.

The agitation system is preferably an ultrasonic agitation (elastic waves of which the frequency is between 15 kHz and a few hundred MHz) implemented by transmission of ultrasound by water in an ultrasonic bath or directly by an ultrasonic transducer (Borthwick et al. (2005) Journal of microbiological methods 60, 207-216; Belgrader et al. (1999) Analytical chemistry 71 (19), 4232-3236).

The ultrasonic bath has a power of between 5 and 100 W/l, preferably 40 W/l, and an effective power of between 50 and 400 W. An ultrasonic bath that can be used for the device according to the invention is the S-line ultrasonic cleaner from the company Fisher Scientific.

The device according to the invention can optionally comprise an ultrasonic agitation system and another noninvasive system for agitation of the functionalized magnetic beads.

The magnetic field is produced by a permanent magnet or electromagnet.

By way of nonlimiting example, it is possible to use a magnet having the dimensions l×w×d=20×13×10 mm and having, as characteristics, a neodymium-iron-boron (NdFeB) magnetization grade N38 and a nickel/copper/nickel coating.

The characteristics of the electromagnets are, for example, the following: electromagnets drawing 12Vcc 10 W and 1.8 mm stroke.

When a permanent magnet is used, it must be able to be positioned both in proximity to the reaction chamber so as to attract the functionalized magnetic beads (ON position) and at a sufficient distance from the reaction chamber so as to no longer exert any force of attraction on the beads (OFF position); the passage between these two positions can be obtained by various means of moving the permanent magnet.

When an electromagnet is used, it is positioned against or in proximity to the reaction chamber and is either in the operating (ON) mode in order to attract the functionalized magnetic beads, or inactive (OFF), it then no longer exerts any force of attraction on the functionalized magnetic beads.

The efficiency of magnetic attraction of the functionalized magnetic beads by the magnet or the electromagnet can be improved by adding to the reaction chamber a metal foam as described in U.S. Pat. No. 6,159,378, preferably nickel metal foams.

The magnetic beads are usually microspheres having a diameter ranging from one nanometer to a few micrometers; preferably, the functionalized magnetic beads used in the device according to the invention have a diameter of between 0.5 and 10 µm, and more preferably a diameter of 1 µm. Care will be taken to select beads of a size greater than or equal to that of the biological or chemical target(s).

The magnetic nature of the beads makes it possible to control them in a container using a magnet. The beads do not have a magnetic property in the absence of an external magnetic field, thereby avoiding the formation of aggregates and allowing reuse thereof.

Magnetic beads of any type known to those skilled in the art can be used in the device according to the invention; in this respect, mention may be made of the functionalized magnetic beads sold by the companies Dynal or Chemicell.

Mention may also be made of the functionalized magnetic beads for capturing biological targets described in U.S. Pat. No. 4,628,037.

The magnetic beads are functionalized, i.e. their external surface is coated with molecules having the property of binding more or less specifically with one or more biological or chemical targets; these molecules are called capture material. The surface area of the beads coated with the capture material constitutes the capture surface area. Preferably, this capture surface area is between $1 \times 10^{-2}$ and $10 \times 10^{-2}$ m$^2$.

Various types of bonds between the capture material and the targets may be involved:
- electrostatic interactions: the targets are captured according to the charges present at their surface. The capture surfaces contain anion-exchange or cation-exchange end groups of more or less large force. They may be carboxyl, sulfone, phosphate, diethylamino-ethyl (DEAE), polylysine, polyethyleneimine (PEI) and more generally charged polymers (Deponte et al. Anal. Bioanal. Chem. 2004; 379: 419-426);
- hydrophobic interactions: the targets are captured according to the difference in hydrophobicity of the surfaces. For example, the hydrophobic regions of targets such as proteins, peptides or nucleic acids in an aqueous medium bind preferentially to a hydrophobic capture material such as a hydrocarbon-based chain containing 1 (methyl) to 18 (octadecyl) carbon atoms;
- covalent bonds: functional end groups grafted onto the beads make it possible to covalently bond the target ligands; they are in particular amine, hydroxyl, thiol, polyglutaraldehyde, etc., groups;
- affinity bonds: the beads are coated with ligands which allow highly specific and selective bonds such as interactions between an antigen and an antibody, a hybridization between two nucleotide fragments, between biotin and streptavidin, etc. (Ergin et al. Microbial Cell Factories 2007; 6: 18; Steingroewer et al., J. Magnetism Magnet. Material 2007; 311: 295-299; Aim et al., J. of Virology 2005 79(1): 622-625).

The choice of the capture material is made according to the biological or chemical target(s) sought.

According to one variant of the device according to the invention, the magnetic beads are functionalized with two or more different capture materials allowing the capture of two or more targets. Either magnetic beads coated with several different capture materials are used, or several types of magnetic beads are used, each type of beads being coated with a different capture material.

The functionalized magnetic beads are fed into the reaction chamber in an amount such that the ratio between the capture surface and the volume of the sample is between 0.2 and 200 m$^2$/l, preferably between 0.2 and 20 m$^2$/l, more preferably between 0.5 and 10 m$^2$/l and most preferentially between 1 and 5 m$^2$/l, for example 2.8 m$^2$/l.

By way of example, in the case of beads 1 μm in diameter, functionalized with PEI (Chemicell), a number of beads of between $9 \times 10^8$ and $9 \times 10^9$, representing a capture surface of between $2.83 \times 10^{-3}$ m$^2$ and $2.83 \times 10^{-2}$ m$^2$, may be used.

The device according to the invention has the advantage of allowing the processing of liquid samples of large volume, greater than or equal to 10 ml, preferably greater than or equal to 50 ml and more preferentially greater than or equal to 500 ml, while at the same time keeping a reaction chamber of small size (a maximum of a few milliliters) thus making it possible to retain the advantages of a capture of biological or chemical targets in a small volume, i.e.:
- less space taken up by and low cost of the device by virtue of its small size;
- easier and faster recovery of the magnetic beads;
- greater ease of dispersion and of mixing of the magnetic beads;
- decrease in the volume of reagents required and in the time devoted to processing the magnetic beads after capture;
- increase in target detection sensitivity;
- high concentration of targets captured.

This device is also advantageous in that it offers a good capture surface to reaction chamber volume ratio and a large range of capture materials chosen according to the biological or chemical targets sought; finally, the functionalized magnetic beads can be recovered and reused.

The automated processing of liquid samples of large volumes by the device according to the invention advantageously replaces the usual techniques for processing samples of this type, such as filtration or ultrafiltration.

This device thus makes it possible to take a fraction of a sample that may contain biological or chemical targets, to capture said targets and to concentrate in order to process them so as to confirm or even quantify their presence.

Thus automated, this device can be placed at the site of the sampling in order for it to take regular samples and to carry out regular analyses.

Figure 2:
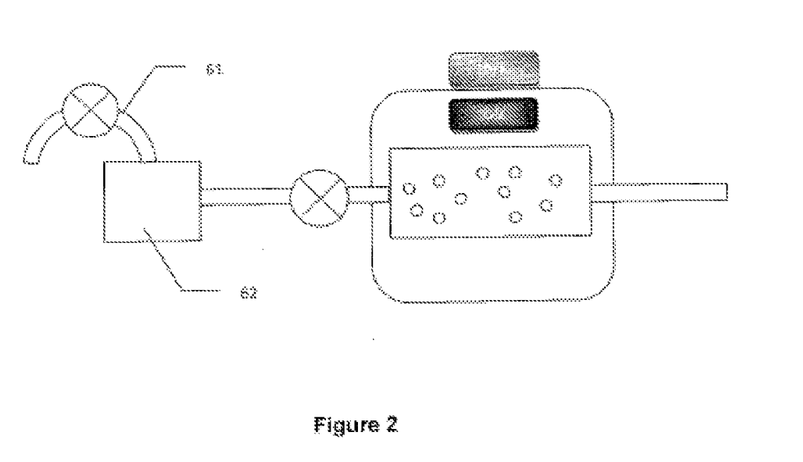
FIG. 2 is a diagrammatic representation of a device that is in accordance with the present invention that is supplemented with a liquid-sample collecting system.

The device according to the invention can be supplemented with a liquid-sample collecting system consisting of a fluidic system for taking the sample (61), such as a pump, and of a storage reservoir (62) for the sample upstream of the reaction chamber (FIG. 2). The liquid-sample collecting system is connected either directly, or via one or more intermediate reservoirs, to the fluid movement system allowing a fraction of the liquid sample to be fed into the reaction chamber (51).

The present invention also relates to a method for capturing biological or chemical targets that may be present in a liquid sample having a volume V greater than or equal to 10 ml, preferably greater than or equal to 50 ml and more preferentially greater than or equal to 500 ml, using a device according to the invention, comprising the steps of:
a) taking a fraction of volume v of said liquid sample;
b) bringing said fraction into contact with functionalized magnetic beads in the reaction chamber of said device where the magnetic field is deactivated;
c) homogeneously dispersing the beads by means of the noninvasive agitation system for a period of at least 5 seconds, preferably between 15 seconds and 10 minutes, more preferably of approximately 30 seconds;
d) capturing the beads by means of the activated magnetic field;
e) discharging said fraction;
f) repeating steps a) to e) a number of times n such that n is between 1 and V/v, preferably n=V/v.

The automation of the method according to the invention is programmed and controlled by a suitable computer system.

The processing of the biological or chemical targets captured on the functionalized magnetic beads can be carried out in the reaction chamber of the device according to the invention or else in a reservoir connected to the fluid movement system allowing discharging of the contents of the reaction chamber (52).

In the case of biological targets, this processing consists of:
- elution of the biological targets by means of an elution buffer that those skilled in the art will choose according to said target, then biological or biochemical analysis of the targets thus eluted.

The biological or biochemical analysis can, for example, consist in the culturing, on selective media, of the eluted biological targets when they are micro-organisms, and the characterization thereof; or else the detection with antibodies of the biological targets, etc.

According to one preferred variant, the eluted biological targets are lysed in order to release their nucleic acids. The lysis methods are widely known to those skilled in the art; they may be a chemical lysis using a lysis buffer containing detergents such as sodium dodecyl sulfate (SDS), lithium dodecyl sulfate (LiDS) or sarkosyl, or chaotropic agents such as guanidium hydrochloride (GHCl), guanidium thiocyanate (GTC), sodium iodide (NaI), perchlorate, etc., an enzymatic lysis using proteinase K or lysozyme, etc., or else a mechanical lysis, for example by coupling the effect of the beads and of the ultrasound or by means of a thermal gradient. The nucleic acids obtained are then analyzed, for example by PCR or hybridization.

According to this variant, a second step of purifying and concentrating the nucleic acids obtained can also be carried out with the device according to the invention comprising functionalized magnetic beads using a capture material for nucleic acids.

In the case of chemical targets, the processing consists of:
elution of the chemical targets using an elution buffer that those skilled in the art will choose according to said target, then
analysis of the recovered targets by conventional chemical techniques such as nuclear magnetic resonance, chromatography, UV or IR spectroscopy, electrochemistry, etc.

When the targets are biochemical in nature, the detection is carried out by means of the techniques at the disposal of those skilled in the art, that they choose according to the biochemical target, for example coupling of the target with an antigen labeled radio-actively or by fluorescence, etc.

Thus, the invention also relates to a method for detecting biological or chemical targets, comprising steps a) to f) of the capture method above, characterized in that it also comprises steps: g) of eluting said targets; and h) of detecting said targets eluted in step g).

When the detection method according to the invention is aimed at biological targets, step h) can consist in lysing said targets and in detecting the nucleic acids released during the lysis.

In addition to the above arrangements, the invention also comprises other arrangements that will emerge from the description which follows, which refer to examples of implementation of the present invention, and also to the appended figures in which:

FIG. 1 is a diagrammatic representation of the device according to the invention.

FIG. 2 is a diagrammatic representation of the device according to the invention comprising, in addition, a liquid-sample collecting system.

Figure 3:
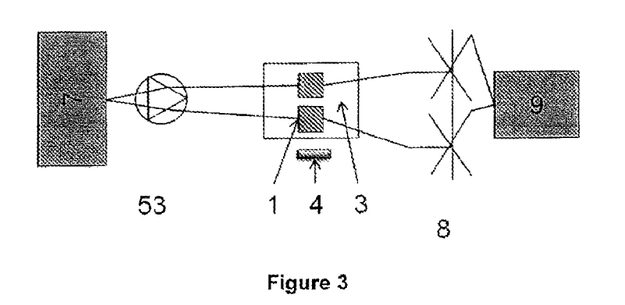
FIG. 3 illustrates the assembly of a device according to the invention used in the examples.
Figure 4:
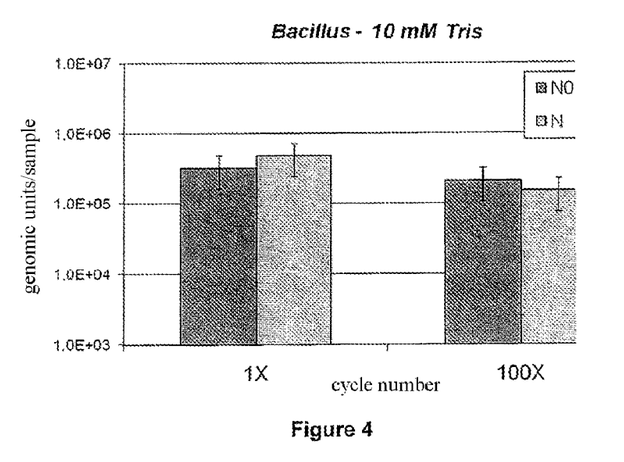
FIGS. 4 to 7 are histograms representing and comparing the amount of genomic units identified in samples according to a method of the invention (N) or initially present in the samples (N0).
Figure 5:
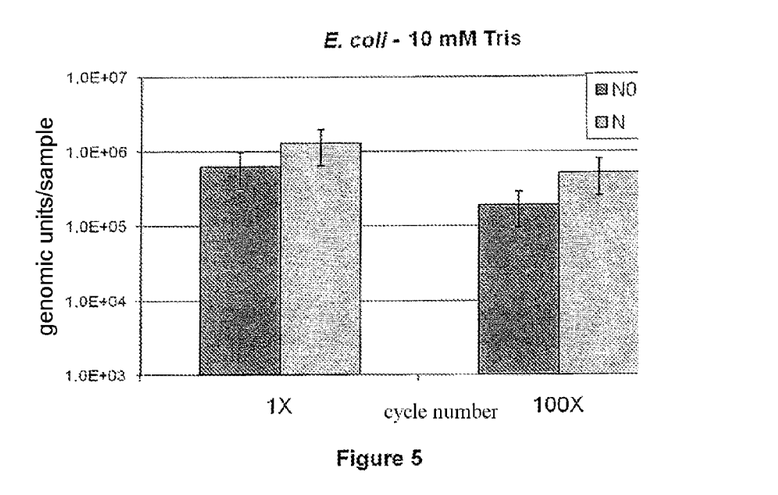
Figure 6:
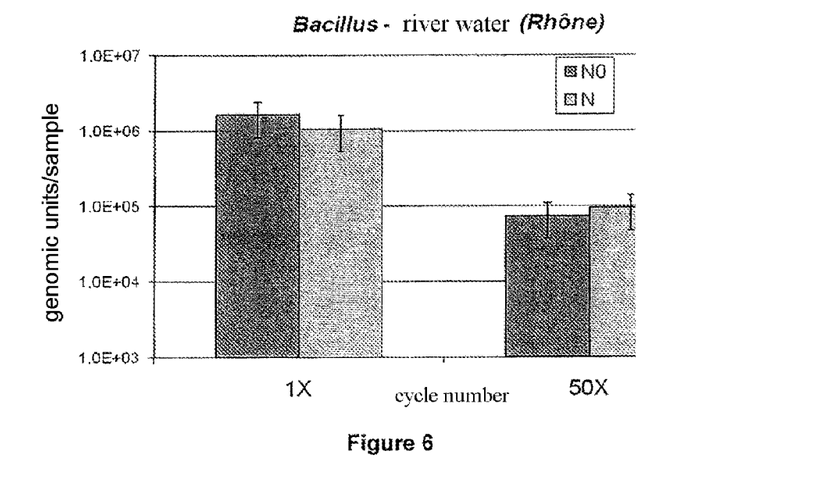
Figure 7:
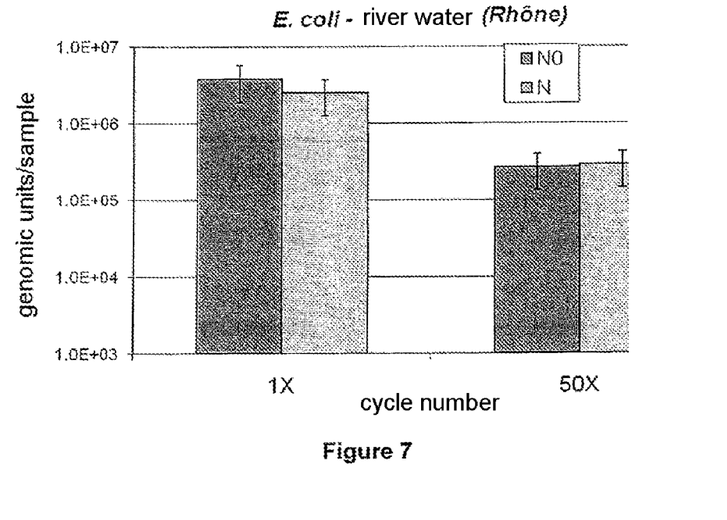

FIG. 3 illustrates the assembly of the device according to the invention used in the example which follows; said device comprises two identical assemblies in parallel, each consisting of a reaction chamber (1); the two reaction chambers are placed in an ultrasonic bath (3) equipped with a magnet (4); they are connected, on the one hand, to a waste container (7) via a pump (53) and, on the other hand, to a reservoir (9) containing the sample, the reaction chambers being fed with sample by means of solenoid valves (8).

FIGS. 4 to 7 are histograms representing and comparing the amount of genomic units identified in samples according to the method of the invention (N) or initially present in the samples (N0).

EXAMPLE

Capture of Bacteria in a Sample of River Water

Instrumentation

Two identical devices were placed on parallel paths (FIG. 3).

The circulation of the fluids is provided by an Ismatec IPC-N peristaltic pump connected to flexible PFA tubes having an external diameter of 1.6 mm and an internal diameter of 1 mm. These flexible tubes act as a reaction chamber in which the magnetic beads are stored.

The beads are controlled by a magnet. The position of the magnet is controlled by the arm of an electro-magnet; in its ON position, the magnet is in contact with the flexible tube; in the OFF position, it is distanced therefrom.

The region of the flexible tube serving as a reaction chamber and where the beads are positioned is immersed in an ultrasonic bath, the function of which is to disperse the aggregates formed by the beads after their capture in the magnetic field.

Downstream, the flexible tube is connected to a 6-way valve (Upchurch V-1471-DC) making it possible to select the liquid entering.

The control of all these components is automated and carried out by means of LabView software from the company Nation Instrument.

Operating Principle of the Instrumentation for the Capture of Targets in a Volume of 20 ml The complete sample having a volume V of 20 ml is stored in a reservoir.

An amount equivalent to a volume of 10 µl, i.e. $1.8 \times 10^8$ beads 1 µm in diameter, is fed into the flexible tube at the level of the magnet in the ON position.

A fraction having a volume v of 100 µl is taken from the sample with the pump.

This volume v is positioned in the flexible tube at the level of the beads; the magnet is then placed in the OFF position; the ultrasound is turned on and enables dispersion of the beads in the fraction of volume v.

The ultrasound is then turned off; the sample is moved in the flexible tube with the aim of resuspending the beads possibly deposited on the wall via the action of the ultrasound.

The beads are left in contact with the sample for 45 seconds, allowing capture of the targets.

The magnet is then placed in the ON position, the beads are then captured by the magnetic field and aggregate against the inner wall of the flexible tube. The sample is pushed by the pump in the direction of a waste container at a speed of 300 µl/min, and a new fraction of volume v of the sample is positioned in the reaction chamber where the beads are to be found.

This capture cycle is repeated 50 to 100 times.

Elution of Targets

Since the system comprises several valves, it is possible to select a new entry connected to a reservoir containing the elution buffer (or even lysis buffer if necessary). This buffer is positioned, via the action of the pump, at the level of the bead storage region.

The magnet being in the OFF position, the ultrasound is applied in order to disperse the beads in the buffer. The targets are then eluted from the surface of the beads and optionally lysed.

The magnet is then placed in the ON position; the beads aggregate and are retained, while the sample of elution and, optionally, lysis buffer comprising the targets is recovered by virtue of the pump.

Detailed Protocol

The principle of this capture was carried out on two liquid samples, one of 20 ml of 10 mM Tris-HCl buffer, pH 8, and the other of 10 ml of a river water (Rhône) taken that very day; these two samples were doped with targets: *Escherichia coli* and *Bacillus subtilis* cells at approximately $10^6$ genomic units (corresponds to approximately $10^6$ bacteria).

The magnetic beads used are superparamagnetic beads coated with a layer of polyethyleneimine (SiMAG-PEI Chemicell) which allows electrostatic-type interactions with the targets (bacterial cells); this is because the bacteria have an overall negative charge and PEI is a strong anion exchanger. The bead surface/sample fraction volume ratio is 2.8 m²/l.

In order to take the 20 ml of 10 mM Tris-HCl, pH 8, it is necessary to carry out 100 cycles of 100 μl on the two devices mounted in parallel. According to the same calculation, it will be necessary to carry out 50 cycles in order to process the 10 ml of river water.

In order to evaluate the efficiency of this capture system, $10^6$ genomic units are added to 100 μl of the samples prepared, which are treated in one cycle in order to obtain a reference capture efficiency.

At the end of the capture cycle, the beads are recovered in 100 μl of 10 mM Tris-HCl. The DNA extraction is then carried out directly on the beads: the cell lysis is carried out at 37° C. in a lysis buffer (5M of guanidine-HC, 20 mM of Tris, pH 8, 1% sarkosyl). After incubation for 10 minutes, the mixture is placed in an ultrasonic bath at 37° C. for two minutes. The beads are grouped together using a magnet and the supernatant is recovered and placed in 4 times its volume of solution containing 3M guanidine-HCl, 20 mM Tris-HCl, 80% (v/v) ethanol, pH 4; the DNA is then captured on 2.5 μl of silanol-functionalized magnetic beads (SiMAG-Silanol, Chemicell). After two rinses with a solution of 2 mM NaCl, 10 mM Tris-HCl, 75% (v/v) ethanol, the purified DNA is eluted in 10 μl of 10 mM Tris-HCl, pH 8, after 2 minutes in an ultrasonic bath.

The DNA extraction and purification protocol can also be carried out automatically with the instrumental device having been used for the previous capture step.

The amount of DNA extracted (N) is determined by quantitative PCR and is expressed in genomic units. For this, 5 μl of extracted DNA suspension are mixed with 5 μl of the following PCR reagents: 0.3 μM primers, 2.5 U Gold Taq polymerase, BSA (1.4 mg/ml), 1× buffer (supplied with the AmpliTaq Gold® DNA Polymerase from Applied Biosystems), 3M MgCl$_2$, 200 μM dNTP, 0.65 mM betaine.

The primers used have the sequence:

```
    Escherichia coli (16S ribosomal RNA gene)

ColiTQF Forward  5'-CATGCCGCGTGTATGAAGAA coliTQR Reverse  5'-CGGGTAACGTCAATGAGCAAA Probe            5'-TATTAACTTTACTCCCTTCCTCCCCGCTGAA Bacillus subtilis (16S ribosomal RNA gene)

BacFbis Forward  5'-ACGTGGGTAACCTGCCTGTAAG
        bis

BacRbis Reverse  5'-TAGCCGAAGCCACCTTTTATGT
        bis

Probe            5'-TACCGGATGGTTGTTTGAACCGCATGGT
```

The number of genomic units initially present in the sample (N0) is determined by PCR by mixing 5 μl of the initial liquid sample, previously subjected to ultrasound for 10 minutes, with 5 μl of the mixture of PCR reagents described above.

Results

Detection of Targets in the Samples of Tris-HCl Buffer

The results obtained (FIGS. 4 and 5) show that the differences observed between the amount of DNA captured by the device according to the invention (N) and the amount of DNA present in the corresponding initial sample (N0) are less than 0.4 log 10, which means that virtually all of the cells initially present were captured.

Detection of Targets in the Samples of River Water

In the same way, the results obtained (FIGS. 6 and 7) show that the differences observed between the amount of DNA captured by the device according to the invention (N) and the amount of DNA present in the corresponding initial sample (N0) are less than 0.2 log 10, which here again shows that virtually all of the cells initially present were captured.

The invention claimed is:

1. An automatic device for processing a liquid sample having a volume V greater than or equal to 10 ml, comprising a reaction chamber, having a volume v of between 10 µl and 5 ml, in which functionalized magnetic beads are placed, said beads having a diameter between 0.5 and 10 µm and allowing the capture of biological or chemical targets in an amount such that the ratio of the capture surface area of the beads to the volume of the reaction chamber is between 0.2 and 200 m$^2$/l, wherein said capture surface area of the beads is between $1 \times 10^{-2}$ and $10 \times 10^{-2}$ m$^2$, said reaction chamber being equipped:

with a noninvasive agitation system enabling homogeneous dispersion of said beads;

with a magnetic field that can be activated or inactivated; and with a fluid movement system for feeding and discharging a portion or the entirety of the contents of the reaction chamber.

2. The device as claimed in claim 1, wherein the reaction chamber has a volume between 50 and 500 µl.

3. The device as claimed in claim 1, wherein the reaction chamber is coated with a hydrophobic surface chosen from Teflon, ethylene trifluoroethylene (ETFE), perfluoroalkoxy (PFA) and polytetrafluoroethylene (PTFE).

4. The device as claimed in claim 1, wherein said noninvasive agitation system is an ultrasonic agitation system.

5. The device as claimed in claim 1, wherein said magnetic field is produced by a permanent magnet or an electromagnet.

6. The device as claimed in claim 1, wherein said functionalized magnetic beads have a diameter between 0.5 and 10 µm.

7. The device as claimed in claim 1, wherein the device also comprises a liquid-sample collecting system consisting of a fluidic system for taking the sample, and a storage reservoir upstream the reaction chamber.

8. A method for capturing biological or chemical targets in a liquid sample having a volume V greater than or equal to 10 ml, with the device as claimed in claim 1, comprising the steps of:

a) taking a fraction of volume v of said liquid sample;

b) bringing said fraction into contact with functionalized magnetic beads in the reaction chamber of said device when the magnetic field is inactivated;

c) homogeneously dispersing the beads using the noninvasive agitation system for a period of at least 5 seconds, wherein said functionalized magnetic beads are capable of binding to said biological or chemical targets;

d) capturing the beads using an activated magnetic field;

e) discharging said fraction; and f) repeating steps a) to e) a number of times n wherein n is between 1 and V/v, thereby said biological or chemical targets in said liquid sample are captured on the magnetic beads.

9. The method as claimed in claim 8, wherein n=V/v.

10. A method for detecting whether biological or chemical targets are present in a liquid sample having a volume V greater than or equal to 10 ml, with the device as claimed in claim 1, comprising the steps of:

a) taking a fraction of volume v of said liquid sample;

b) bringing said fraction into contact with functionalized magnetic beads in the reaction chamber of said device when the magnetic field is inactivated;

c) homogeneously dispersing the beads using the noninvasive agitation system for a period of at least 5 seconds, wherein said functionalized magnetic beads are capable of binding to said biological or chemical targets;

d) capturing the beads using an activated magnetic field;

e) discharging said fraction;

f) repeating steps a) to e) a number of times n wherein n is between 1 and V/v such that the biological or chemical targets in said liquid sample are captured on the magnetic beads if the biological or chemical targets are present in said liquid sample;

g) washing the beads captured in step f) with an eluent, thereby producing an eluted solution; and h) detecting whether the biological or chemical targets are present in said liquid sample by analyzing the eluted solution.

11. The method for detecting biological targets as claimed in claim 10, wherein step h) consists of lysing said targets and detecting the nucleic acids released during the lysis if the targets are present in said liquid sample and said targets are microorganisms.

12. The device as claimed in claim 2, wherein the reaction chamber has a volume of approximately 100 µl.

13. A method for capturing biological or chemical targets in a liquid sample having a volume V greater than or equal to 10 ml, with the device as claimed in claim 1, comprising the steps of:

a) taking a fraction of volume v of said liquid sample;

b) bringing said fraction into contact with functionalized magnetic beads in the reaction chamber of said device when the magnetic field is inactivated;

c) homogeneously dispersing the beads using the noninvasive agitation system for a period of at least 5 seconds, wherein said functionalized magnetic beads are capable of binding to said biological or chemical targets;

d) capturing said functionalized magnetic beads;

e) activating a magnetic field so that the magnetic beads are aggregated on a wall of the reaction chamber; and f) discharging said fraction; and g) repeating steps a) to f) a number of times n wherein n is between 1 and V/v thereby said biological or chemical targets in said liquid sample are captured on the magnetic beads.

* * * * *